United States Patent

Wefler et al.

[19]

[11] Patent Number: 6,123,935
[45] Date of Patent: Sep. 26, 2000

[54] AIR FRESHENER DISPENSER DEVICE WITH DISPOSABLE HEAT-ACTIVATED CARTRIDGE

[75] Inventors: Mark E. Wefler, Mount Pleasant; John Martin, Caledonia, both of Wis.

[73] Assignee: S. C. Johnson & Son, Inc., Racine, Wis.

[21] Appl. No.: 08/837,517

[22] Filed: Apr. 14, 1997

[51] Int. Cl.[7] .................................................. A61L 9/03
[52] U.S. Cl. ..................... 424/76.1; 424/76.2; 424/76.3; 424/76.4; 239/44; 239/45; 239/50; 392/392.2
[58] Field of Search ............................ 424/76.1, 76.2, 424/76.3, 76.4; 239/44, 45, 50; 392/392.2

[56] References Cited

U.S. PATENT DOCUMENTS

| | | | |
|---|---|---|---|
| 1,994,932 | 3/1935 | Vidal | 99/18 |
| 2,597,195 | 5/1952 | Smith | 21/119 |
| 2,802,695 | 8/1957 | Johnson | 299/24 |
| 2,804,291 | 8/1957 | Hard af Segerstad | 261/99 |
| 3,067,310 | 12/1962 | Walz et al. | 219/19 |
| 3,266,661 | 8/1966 | Dates | 220/64 |
| 3,288,556 | 11/1966 | Weber . | |
| 3,431,393 | 3/1969 | Katsuda | 219/274 |
| 3,482,929 | 12/1969 | Gentil | 21/53 |
| 3,550,853 | 12/1970 | Gray | 239/44 |
| 3,633,881 | 1/1972 | Yurdin | 261/24 |
| 4,020,321 | 4/1977 | Oswald | 219/271 |
| 4,037,352 | 7/1977 | Hennart et al. | 43/129 |
| 4,228,124 | 10/1980 | Kashihara et al. | 422/36 |
| 4,286,754 | 9/1981 | Jones | 239/6 |
| 4,314,915 | 2/1982 | Wiegers et al. | 252/522 |
| 4,411,829 | 10/1983 | Schulte-Elte et al. | 252/522 |
| 4,413,779 | 11/1983 | Santini | 239/45 |
| 4,434,306 | 2/1984 | Kobayashi et al. | 568/820 |
| 4,454,987 | 6/1984 | Mitchell | 239/6 |
| 4,849,255 | 7/1989 | Grise et al. | 427/122 |
| 4,849,606 | 7/1989 | Martens, III et al. . | |
| 4,857,384 | 8/1989 | Mio et al. | 428/164 |
| 4,912,306 | 3/1990 | Grise et al. | 219/549 |
| 4,913,350 | 4/1990 | Purzycki . | |
| 4,935,156 | 6/1990 | van Konynenburg et al. | 219/553 |
| 4,968,487 | 11/1990 | Yamamoto et al. . | |
| 5,000,383 | 3/1991 | van der Heijden | 239/47 |
| 5,038,394 | 8/1991 | Hasegawa et al. . | |
| 5,106,540 | 4/1992 | Barma et al. | 252/511 |
| 5,234,162 | 8/1993 | Sullivan | 239/56 |
| 5,242,111 | 9/1993 | Nakoneczny et al. | 239/47 |
| 5,290,546 | 3/1994 | Hasegawa et al. | 424/76.2 |
| 5,364,027 | 11/1994 | Kuhn | 239/44 |
| 5,382,384 | 1/1995 | Baigrie et al. | 252/511 |
| 5,415,934 | 5/1995 | Mori | 428/408 |
| 5,574,821 | 11/1996 | Babasade . | |

FOREIGN PATENT DOCUMENTS

| | | |
|---|---|---|
| 0 689 766 | 1/1996 | European Pat. Off. . |
| 2 432 837 | 3/1980 | France . |
| 2 741 807 | 6/1997 | France . |
| 36 09 511 | 10/1986 | Germany . |
| 41 31 613 | 3/1993 | Germany . |
| 44 46 418 | 6/1996 | Germany . |
| 2 275 608 | 9/1994 | United Kingdom . |
| 94/15650 | 7/1994 | WIPO . |

*Primary Examiner*—Thurman K. Page
*Assistant Examiner*—Brian K. Seidleck

[57] ABSTRACT

This invention provides an air freshener dispenser device comprising (1) a disposable air freshener cartridge which has an affixed electrical-resistance heating element on its upper section surface, and (2) an electrical plug housing. The cartridge has an elongated thermoplastic hollow body configuration with a sealed internal reservoir chamber of liquid air freshener medium, and the upper section of the cartridge body is shaped to a flat shallow extension of the cartridge chamber. A thin wick matrix extends internally from the cartridge chamber bottom up to the top of the chamber shallow extension. The cartridge has an integrally structured means adapted for removal of a top portion of the cartridge chamber shallow extension to expose an upper section of wick matrix to the atmosphere. The electrical plug housing is detachably secured and positioned proximate to the cartridge heating element. Activation of the heating element promotes air freshener dispersion into the atmosphere from the exposed wick.

19 Claims, 2 Drawing Sheets

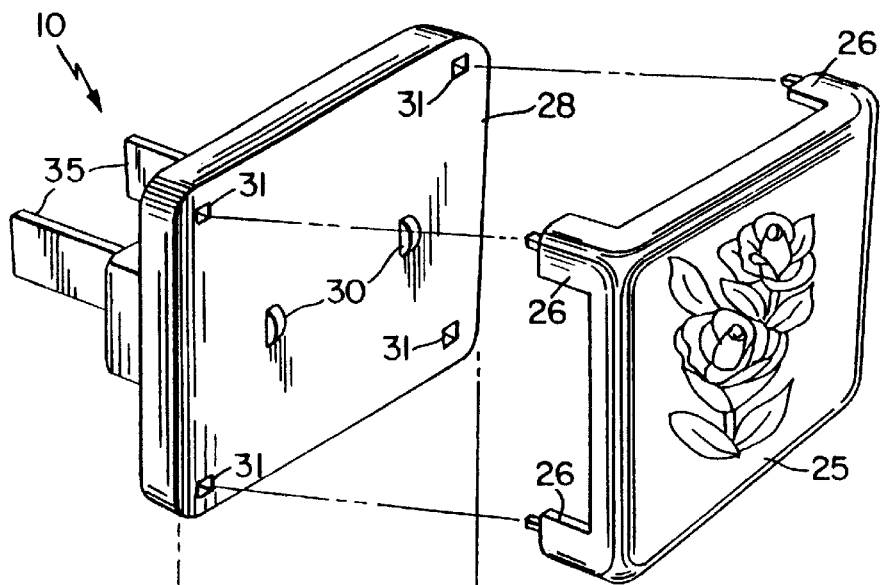
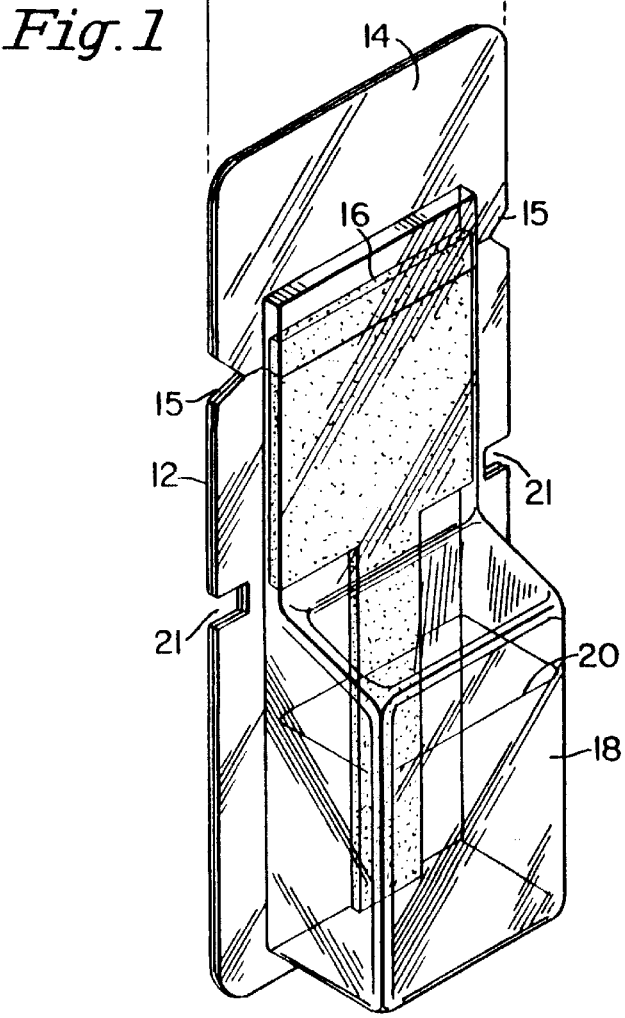
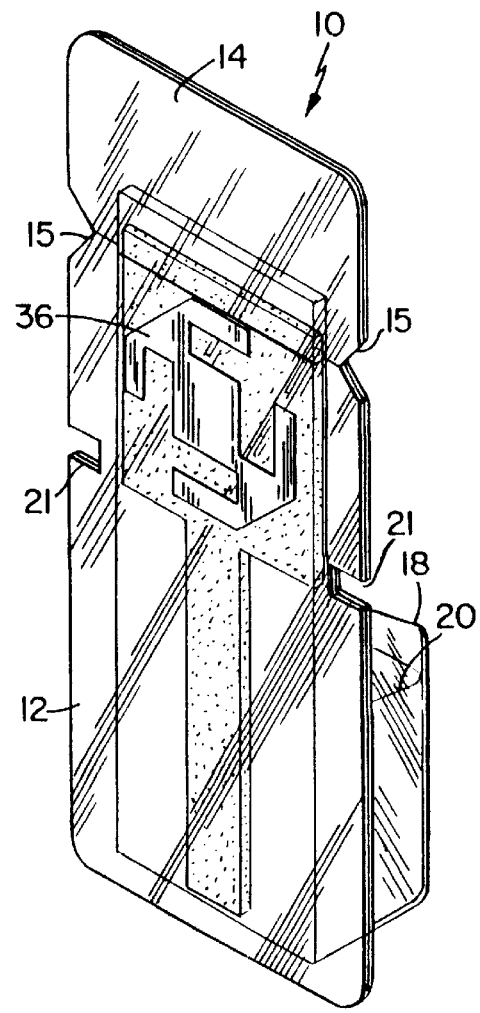
Fig.1
Fig.2

AIR FRESHENER DISPENSER DEVICE WITH DISPOSABLE HEAT-ACTIVATED CARTRIDGE

BACKGROUND OF THE INVENTION

This invention generally relates to dispensers of vaporizable media. More specifically, this invention relates to a device for dispensing a fragrance or deodorant in the form of a vapor for air freshening in an enclosed environment.

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks are also used for dispensing air-treating vapors into the atmosphere by evaporation. Another group of vapor-dispensing devices utilizes a carrier material such as paperboard impregnated or coated with a vaporizable composition.

A number of recent developments include a liquid air-treating composition in an enclosure, all or part of which is formed of a polymeric film through which the air-treating composition can migrate to be released as a vapor at an outer surface. Use of this type of permeable polymeric membrane controls the dispensing of air-treating vapors and tends to eliminate great variations in the rate of dispensing over the life of the product.

Wicking devices are well known for dispensing volatile liquids into the atmosphere, such as fragrance, deodorant, disinfectant or insecticide active agent.

A typical wicking device utilizes a combination of a wick and emanating region to dispense a volatile liquid from a liquid reservoir. Wicking devices are described in U.S. Pat. Nos. 1,994,932; 2,597,195; 2,802,695; 2,804,291; 3,550,853; 4,286,754; 4,413,779; 4,454,987; 4,913,350; and 5,000,383; incorporated by reference.

Of special interest with respect to the present invention are wicking dispenser devices in which the wicking action is promoted by a heat source. This type of wicking device is described in U.S. Pat. Nos. 3,288,556; 3,431,393; 3,482,929; 3,633,881; 4,020,321; 4,968,487; 5,038,394; 5,290,546; and 5,364,027; incorporated by reference.

Some air freshener dispensers are expensive to manufacture. Other air freshener dispensers are inexpensive to produce, but tend to have inferior construction and functionality.

There remains a need for a well-constructed air freshener dispenser device which can be mass-produced economically and which can deliver a vapor medium at a controlled uniform rate over an extended period of time.

Accordingly, it is an object of this invention to provide an improved air freshener dispenser device for delivering an odorant and/or deodorant vapor in an enclosed environment.

It is another object of this invention to provide an air freshener dispenser device with a primary structure which is a plastic assembly that can be produced economically by a thermoforming means.

It is another object of this invention to provide a disposable air freshener dispenser device which has an interactive combination of an electrical plug and an air freshener cartridge unit having an affixed heating element.

It is a further object of this invention to provide an air freshener cartridge for utility in a heat-activated air freshener dispenser device, wherein the cartridge has an internal air freshener reservoir in contact with a wicking means.

Other objects and advantages of the present invention shall become apparent from the accompanying description and drawings.

SUMMARY OF THE INVENTION

One or more objects of the present invention are accomplished by the provision of a disposable air freshener dispenser device which is adapted for engagement and support by an electrical outlet, and which is an assembly of structural units comprising:

(1) a disposable cartridge having
  (a) an elongated thermoplastic hollow body configuration with a sealed internal reservoir chamber of liquid air freshener medium, and the upper section of the cartridge body is shaped to a flat shallow extension of the cartridge chamber;
  (b) a thin wick matrix which extends internally from the cartridge chamber bottom up to the top of the chamber shallow extension;
  (c) integrally structured means adapted for removal of a top portion of the cartridge chamber shallow extension to expose an upper section of wick matrix to the atmosphere; and
  (d) an electrical-resistance heating element means which is affixed to the back surface of the said cartridge chamber shallow extension; and (2) an electrical plug housing which is detachably secured and positioned proximate to the heating element affixed to the back surface of the cartridge chamber shallow extension, wherein the electrical plug housing has two metal prongs which extend forwardly to contact the said heating element, and extend rearwardly from the plug housing for engagement with an electrical outlet and for conduction of an electric current to the said heating element, whereby air freshener wicking into the atmosphere is heat-promoted.

In another embodiment this invention provides a disposable air freshener cartridge which is adapted for utility as a module in a heat-activated air freshener dispenser device, wherein the cartridge structure comprises:

(a) an elongated thermoplastic hollow body configuration with a sealed internal reservoir chamber of liquid air freshener medium, and the upper section of the cartridge body is sloped to a flat shallow extension of the cartridge chamber;

(b) thin wick matrix which extends internally from the cartridge chamber bottom up to the top of the chamber shallow extension;

(c) integrally structured means adapted for removal of a top portion of the cartridge chamber shallow extension to expose an upper section of the wick matrix to the atmosphere;

(d) an electrical-resistance heating element means which is affixed to the back surface of the said cartridge chamber shallow extension.

BRIEF DESCRIPTION OF THE DRAWINGS

FIG. 1 is a composite perspective view of an invention air freshener dispenser device.

FIG. 2 is a perspective back view of an invention disposable air freshener cartridge.

DESCRIPTION OF THE PREFERRED EMBODIMENTS

Figure 3:
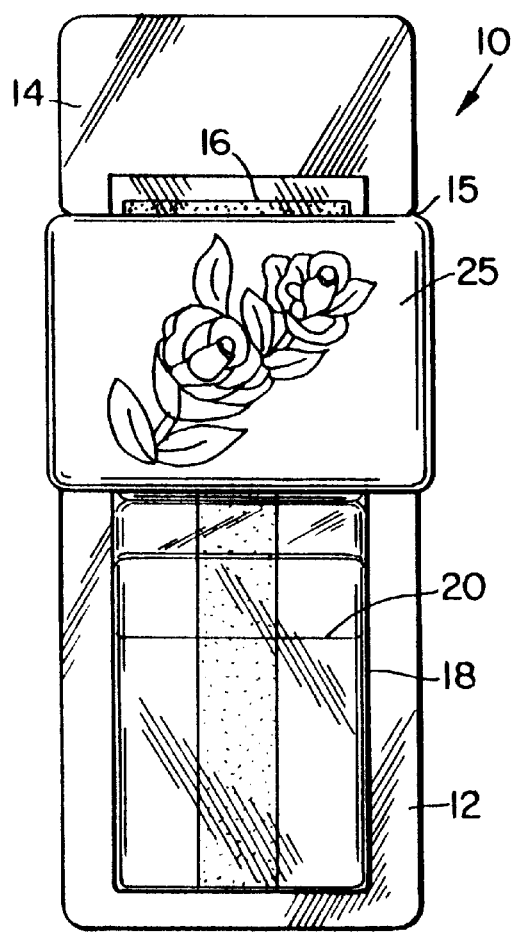
FIG. 3 is an elevational front view of a FIG. 1 invention air freshener dispenser device in assembled form.

FIG. 1 illustrates an exploded view of present invention air freshener dispenser device 10 which consists of an electrical plug, a protective cover, and a disposable air freshener cartridge.

In assembled form, air freshener dispenser device 10 is plugged into a wall electrical outlet by means of twin metal prongs 35 of electrical plug housing 28. Metal prongs 35 are connected to metal contact points 30 located on the front surface of electrical plug housing 28.

Electrical plug housing 28 typically is a plastic structure formed by molding means from a thermoset polymer such as phenol-formaldehyde resin, epoxy resin, polyphenylene sulfide, polyphenylene oxide, polycarbonate, polyimide, polybenzimidazole, and the like, or a thermoplastic polymer such as polyethylene, polypropylene, polyamide, and the like. Protective cover 25 in FIG. 1 can be molded from the same type of polymers as electrical plug housing 28. Both protective cover 25 and electrical plug housing 28 are reusable and capable of long term service.

Protective cover 25 is adapted to engage recesses 31 of electrical plug housing 28 by means of vertical posts 26 of protective cover 25. Optionally, protective cover 25 has vertical posts 26 with insert locking means which engage recesses 31, so that protective cover 25 is permanently affixed to electric plug housing 28 after assembly.

A novel aspect of air freshener dispenser device 10 in FIG. 1 is the structural design of disposable cartridge 12. As illustrated in FIG. 1, cartridge 12 is a construction of sealed juxtapositioned sections of molded vapor-impermeable polyvinyl thin film having transparency. Typically, cartridge 12 is a translucent or transparent structure which is injection or thermoform molded from a polymer such as polyethylene, polypropylene, polystyrene, polyvinyl chloride, polyvinyl acetate, polyamide, polyacrylamide, polymethacrylate, and the like.

Cartridge 12 has notches 21 which can secure cartridge 12 between bottom positioned posts 26 of protective cover 25 when air freshener dispenser device 10 is in assembled form.

Hollow body 18 of cartridge 12 has a sealed internal reservoir chamber with a content of a liquid or gel air freshener medium 20.

Top portion 14 of cartridge 12 is adapted for removal by manual flexing or twisting along detachment line 15, whereby the upper section of internal wick matrix 16 is exposed to the atmosphere.

Cartridge 12 of air freshener dispenser device 10 as illustrated in FIG. 1 typically has rectangular periphery dimensions between about 1–3 inches in width and 2–6 inches in length.

Wick matrix 16 extends from the top of hollow body 18 to the lower area, where wick matrix 16 is immersed in air freshener medium 20.

Wick matrix 16 can be an organic or inorganic liquid-permeable structure, such as a porous thermoplastic, thermoset, cellulosic or ceramic composition.

Wick matrix 16 also can be in the form of a fibrous aggregate or a grooved nonporous strip. A variety of wick compositions and structures suitable for air freshener dispenser devices are described in U.S. Pat. Nos. 3,431,393; 3,482,929; 3,633,881; 4,020,321; 4,968,487; 5,038,394; and 5,290,546; incorporated by reference.

Air freshener medium 20 in cartridge 12 can be any air treating material which is transported upward through wick matrix 16 by capillary action, and dispersed into the atmosphere in vapor form. Typically air freshener medium 20 is a fragrance or a deodorant formulation in liquid form.

Air freshener medium 20 preferably is a liquid fragrance comprising one or more volatile organic compounds which are available from perfumery suppliers such as Firmenich Inc., Takasago Inc., Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

Air freshener medium 20 also can be a liquid formulation containing a volatile pesticide such as p-dichlorobenzene, or a therapeutic agent such as menthol.

Disposable cartridge 12 in FIG. 1 preferably is constructed of transparent or translucent materials, such that air freshener medium 20 is visible during usage for an indication of the liquid level in the interior reservoir of cartridge 12.

FIG. 2 is a perspective back view of disposable cartridge 12 in FIG. 1. Electrical-resistance heating element 36 is affixed to the back surface of cartridge 12 in proximity to the shallow extension of hollow body 18, and the internally positioned wick matrix 16.

Electrical-resistance element 36 in FIG. 2 can be in the form of a printed electric-conductive ink or electric-conductive polymer coating with electrical-resistance properties for heat generation. Printed or thin film electrical-resistance heating elements are described in publications such as U.S. Pat. Nos. 3,067,310; 3,266,661; 4,849,255; 4,857,384; 4,912,306; 4,935,156; 5,106,540; 5,382,384; and 5,415,934; incorporated by reference.

When air freshener dispenser device 10 is in assembled form as illustrated in FIG. 3, and in engagement with a wall electrical outlet, heating element 36 (as represented in FIG. 2) together with metal contacts 30 in plug housing 28 establish an electric circuit. When plug housing 28 draws electric current from an electrical outlet, heating element 36 functions as a heat source and promotes the dispersion of air freshener medium 20 into the atmosphere from exposed wick matrix 16 in cartridge 12.

Preferably, electrical-resistance heating element 36 is in the form of an electrical conduction pattern which accesses electric current through metal contacts 30, and which permits a vertical cartridge 12 alignment for each orientation of a wall electrical outlet. Metal contacts 30 usually will be in a vertical or horizontal configuration, as determined by the wall electrical outlet orientation. Protective cover 25 is design adapted to secure cartridge 12 in a vertical position for the different wall electrical outlet orientations.

FIG. 3 is an elevational front view of air freshener dispenser device 10 of FIG. 1 in an assembled form. FIG. 3 illustrates the utility of protective cover 25 to secure cartridge 12 in a vertical alignment, and to position heating element 36 (represented in FIG. 2) proximate to metal contacts 30 of plug housing 28 (not shown). After removal of cartridge 12 when air freshener medium 20 is expended, protective cover 25 is re-connected to plug housing 28 as a child-proof shield, when plug housing 28 remains in a wall electrical outlet for later reuse with a refill cartridge 12.

Figure 4:
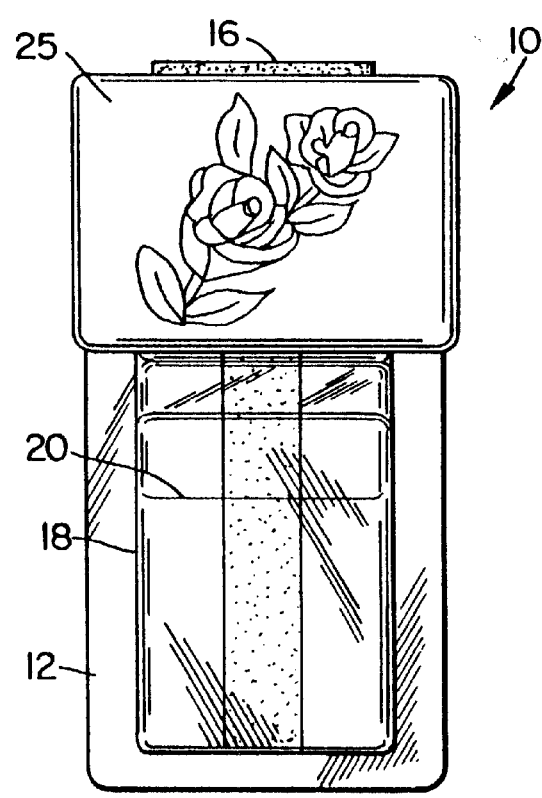
FIG. 4 is an elevational front view of a FIG. 3 invention air freshener dispenser device with an internal wick structure exposed to the environment.

FIG. 4 is an elevational front view of FIG. 3 air freshener dispenser device 10. FIG. 4 illustrates the exposed upper section of wick matrix 16. When air freshener dispenser device 10 is operational, air freshener medium 20 is transported by heat-promoted capillary action up wick matrix 12, and dispersed into the atmosphere as a vapor.

A significant advantage derives from the incorporation of heating element 36 in the structure of disposable cartridge 12. A different heating element 36 can be designed for different air freshener medium 20 formulations. The combination of heating element 36 and specific air freshener medium 20 can be customized for optimum performance.

As a further advantage, a present invention air freshener dispenser device can be produced in high volume from relatively inexpensive plastic materials. After usage, the device qualifies for disposal as a non-hazardous solid waste.

What is claimed is:

1. An air freshener dispenser device which is adapted for engagement and support by an electrical outlet, and which is an assembly of structural units, the dispenser device comprising:
   a disposable cartridge having (a) an elongated thermoplastic hollow body with a sealed internal chamber, the chamber including a reservoir of liquid air freshener medium and an extension extending up from and contiguous with the reservoir; (b) a wick matrix disposed within the reservoir of the cartridge chamber and extending into the chamber extension; (c) integrally structured means for removal of a top portion of the chamber extension to expose an upper section of the wick matrix to the atmosphere; and (d) an electrical-resistance heating element affixed to the back surface of the cartridge body adjacent to the chamber extension; and
   an electrical plug housing which is detachably securable to the cartridge proximate to the heating element, the electrical plug housing including two metal prongs which extend forwardly to contact the heating element when the electrical plug housing is secured to the cartridge, and extend rearwardly from the plug housing for engagement with the electrical outlet to conduct electric current to the heating element, whereby air freshener wicking into the atmosphere is heat-promoted.

2. A dispenser device in accordance with claim 1, wherein the hollow body of the cartridge is a construction of sealed, juxtapositioned sections of molded vapor-impermeable polyvinyl thin film having transparency so that the air freshener medium in the reservoir chamber is visible.

3. A dispenser device in accordance with claim 1, wherein the wick matrix is a porous structure selected from the group consisting of thermoplastic, cellulosic and ceramic compositions.

4. A dispenser device in accordance with claim 1, wherein the air freshener medium is a liquid fragrance composition.

5. A dispenser device in accordance with claim 1, wherein the air freshener medium is a liquid pesticide composition.

6. A dispenser device in accordance with claim 1, wherein the air freshener medium is a liquid therapeutic composition.

7. A dispenser device in accordance with claim 1, wherein the electrical-resistance heating element is one of a film coating and a printed pattern.

8. A dispenser device in accordance with claim 1, wherein the plug housing can be secured to the cartridge with the prongs oriented either horizontally or vertically, and the electrical-resistance heating element is an electrical conduction pattern which contacts the prongs regardless of whether the prongs are oriented horizontally or vertically when the plug housing is secured to the cartridge.

9. A dispenser device in accordance with claim 1, wherein the electrical plug housing is molded from a polymer selected from the group consisting of thermoplastics and thermosets.

10. A dispenser device in accordance with claim 1, further comprising a child-proof shield detachably securable to the plug housing to prevent contact with the forwardly extended metal prongs.

11. A disposable air freshener cartridge for use in a heat-activated air freshener dispenser device, wherein the cartridge comprises:
    (a) an elongated thermoplastic hollow body with a sealed internal chamber, the chamber including a reservoir of liquid air freshener medium and an extension extending up from and contiguous with the reservoir;
    (b) a wick matrix disposed within the reservoir of the cartridge chamber and extending into the chamber extension;
    (c) integrally structured means for removal of a top portion of the chamber extension to expose an upper section of the wick matrix to the atmosphere; and
    (d) an electrical-resistance heating element affixed to the back surface of the cartridge body adjacent to the chamber extension.

12. A plug-in vaporizable medium dispenser, comprising:
    a disposable cartridge, comprising (a) a thermoplastic hollow body comprising detachable top and bottom portions, and a sealed internal chamber, the chamber including (i) a reservoir, located in the bottom portion of the body and in which the vaporizable medium is disposed, and (ii) an extension extending up to the top portion of the body from and contiguous with the reservoir; (b) a wick matrix having a lower portion immersed in the vaporizable medium in the reservoir, and an upper portion extending into the chamber extension, so that detachment of the top portion of the body exposes the upper portion of the wick matrix to the atmosphere; and (c) an electrical-resistance heating element affixed to the bottom portion of the body proximate to the chamber extension; and
    a plug housing detachably securable to the bottom portion of the body of the cartridge, the housing comprising a pair of metal contacts, which engage the heating element of the cartridge when the plug housing is secured to the cartridge, and a pair of metal prongs, electrically connected to the contacts and extending opposite to the contacts from the plug housing for insertion into an electrical outlet to conduct electric current to the heating element via the contacts.

13. A dispenser according to claim 12, wherein the body of the cartridge comprises a plurality of molded, vapor impermeable polyvinyl thin film layers sealed together, at least one of the layers having transparency so that the vaporizable medium in the reservoir is visible.

14. The dispenser device according to claim 12, wherein the wick matrix is formed of a porous material selected from the group consisting of thermoplastics, cellulosic compositions and ceramic compositions.

15. The dispenser device according to claim 12, wherein the vaporizable medium is a liquid selected from the group consisting of fragrances, pesticides and therapeutic agents.

16. The dispenser device according to claim 12, wherein the electrical-resistance heating element comprises one of a thin film coating and a printed pattern.

17. The dispenser device according to claim 12, wherein the plug housing can be secured to the cartridge with the prongs oriented either horizontally or vertically, and the electrical-resistance heating element is an electrically conductive pattern which engages the contacts regardless of whether the prongs are oriented horizontally or vertically when the plug housing is secured to the cartridge.

18. The dispenser device according to claim 12, wherein the plug housing is molded from a polymer selected from the group consisting of thermoplastics and thermosets.

19. The dispenser device according to claim 12, further comprising a child-proof shield detachably securable to the plug housing to prevent contact with the metal contacts.

* * * * *